(12) United States Patent
 Asano

(10) Patent No.: US 10,123,743 B2
(45) Date of Patent: Nov. 13, 2018

(54) MOBILE DEVICE, ACTIVITY CALCULATION SYSTEM, AND CONTROL METHOD AND CONTROL PROGRAM OF MOBILE DEVICE

(71) Applicant: KYOCERA Corporation, Kyoto-shi, Kyoto (JP)

(72) Inventor: Tomoko Asano, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 322 days.

(21) Appl. No.: 14/920,916

(22) Filed: Oct. 23, 2015

(65) Prior Publication Data

US 2016/0038089 A1  Feb. 11, 2016

Related U.S. Application Data

(63) Continuation-in-part of application No. PCT/JP2014/061796, filed on Apr. 25, 2014.

(30) Foreign Application Priority Data

Apr. 26, 2013 (JP) .................................. 2013-093774

(51) Int. Cl.
*A61B 5/00* (2006.01)
*A61B 5/11* (2006.01)
(Continued)

(52) U.S. Cl.
CPC .......... *A61B 5/6898* (2013.01); *A61B 5/1118* (2013.01); *A61B 5/1123* (2013.01); *A61B 5/4866* (2013.01); *A63B 24/0062* (2013.01); *A63B 2024/0071* (2013.01); *A63B 2071/065* (2013.01)

(58) Field of Classification Search
None
See application file for complete search history.

(56) References Cited

U.S. PATENT DOCUMENTS

2006/0064325 A1* 3/2006 Matsumoto ........... A61B 5/1118
 705/3
2010/0256532 A1* 10/2010 Nishibayashi ........ A61B 5/1118
 600/595
2012/0083705 A1* 4/2012 Yuen .................... A61B 5/0002
 600/508

FOREIGN PATENT DOCUMENTS

| JP | 2004-120688 A | 4/2004 |
|----|---|---|
| JP | 2010-17525 A | 1/2010 |
| JP | 2012-61216 A | 3/2012 |

OTHER PUBLICATIONS

Translation for JP 2010-017525 published Jan. 28, 2010.*

(Continued)

*Primary Examiner* — John Kuan
(74) *Attorney, Agent, or Firm* — Hauptman Ham, LLP

(57) ABSTRACT

According to one of aspects, a mobile device, includes: a motion sensor module configured to detect a motion factor; a communication module configured to receive a plurality of operation factors used for an operation of an activity factor indicating an activity amount and respective dates and times at which the operation factors are measured; and a control module configured to calculate the activity factor indicating the activity amount using the operation factors received through the communication module and a value based on the motion factor detected by the motion sensor module when the operation factors are received.

12 Claims, 11 Drawing Sheets

(51) Int. Cl.
*A63B 24/00* (2006.01)
*A63B 71/06* (2006.01)

(56) References Cited

OTHER PUBLICATIONS

Office Action dated Jun. 2, 2015, corresponding to Japanese patent application No. 2013-093774.
International Search Report dated Aug. 5, 2014, corresponding to International application No. PCT/JP2014/061796.
Office Action in JP Application No. 2017-006150 dated Oct. 17, 2017, for which an explanation of relevance is attached. 5pp.

* cited by examiner

MOBILE DEVICE, ACTIVITY CALCULATION SYSTEM, AND CONTROL METHOD AND CONTROL PROGRAM OF MOBILE DEVICE

CROSS-REFERENCE TO RELATED APPLICATION

This application is a Continuation-in-Part of PCT international application Ser. No. PCT/JP2014/061796 filed on Apr. 25, 2014 which designates the United States, incorporated herein by reference, and which is based upon and claims the benefit of priority from Japanese Patent Applications No. 2013-093774 filed on Apr. 26, 2013, the entire contents of which are incorporated herein by reference.

FIELD

Embodiments of the present disclosure relates to a mobile device, an activity calculation system, and a control method and a control program of a mobile device.

BACKGROUND

There is a mobile device having a function of counting the number of steps based on a value detected by an acceleration sensor.

SUMMARY

A mobile device according to an aspect comprises: a motion sensor module configured to detect a motion factor; a communication module configured to receive a plurality of operation factors used for an operation of an activity factor indicating an activity amount and respective dates and times at which the operation factors are measured; and a control module configured to calculate the activity factor indicating the activity amount using the operation factors received through the communication module and a value based on the motion factor detected by the motion sensor module when the operation factors are received.

An activity calculation system according to another aspect comprises: a measuring device; a server; and a mobile device, wherein the measuring device comprises a measuring module configured to measure a plurality of operation factors used for an operation of an activity factor indicating an activity amount, and a first communication module configured to transmit the operation factors measured by the measuring module and respective dates and times at which the operation factors are measured to the server, the server comprises a second communication module configured to receive the operation factors transmitted from the first communication module of the measuring device, and transmit the received operation factors and the respective dates and times at which the operation factors are measured to the mobile device, and the mobile device comprises a third communication module configured to receive the operation factors and the respective dates and times at which the operation factors are measured from the second communication module of the server, a motion sensor configured to detect the motion factor, and a control module configured to calculate the activity factor indicating the activity amount using the operation factors received through the third communication module and a value based on the motion factor corresponding to the date and time corresponding to the operation factor and detected by the motion sensor.

An activity calculation system according to another aspect comprising: a measuring device; and a mobile device, wherein the measuring device comprises a measuring module configured to measure a plurality of operation factors used for an operation of an activity factor indicating an activity amount, and a first communication module configured to transmit the operation factor measured by the measuring module and respective dates and times at which the operation factors are measured, and the mobile device comprises a second communication module configured to receive the operation factors and the respective dates and times at which the operation factors are measured from the first communication module of the measuring device, a motion sensor configured to detect the motion factor, and a controller configured to calculate the activity factor indicating the activity amount using a value based on the motion factor detected by the motion sensor and the operation factor received through the second communication module.

A control method of a mobile device equipped with a motion sensor according to another aspect comprises: receiving a plurality of operation factors used for an operation of an activity factor indicating an activity amount of an activity detected by the motion sensor; and calculating the activity factor indicating the activity amount using the received operation factors and a value based on the motion factor corresponding to the date and the time corresponding to the operation factor and detected by the motion sensor.

A computer program product having computer instructions, stored on a non-transitory computer readable storage medium, for enabling a computer of a mobile device including a motion sensor, a communication module, and a controller executing the computer instructions to perform operations according to another aspect comprises: causing the communication module to receive a plurality of operation factors used for an operation of an activity factor indicating an activity amount of an activity detected by the motion sensor and respective dates and times at which the operation factors are measured; and causing a controller to calculate the activity factor indicating the activity amount using the operation factors received through the communication module and a value based on the motion factor detected by the motion sensor module when the operation factors are received.

DESCRIPTION OF EMBODIMENTS

Exemplary embodiments for carrying out mobile devices of the present disclosure will be described in detail with reference to the appended drawings. In the following description, smartphones are described as exemplary mobile devices.

In a mobile device having a function of counting the number of steps based on a value detected by an acceleration sensor, it may be needed to use a detected walk effectively.

It is an object of the present disclosure to provide a mobile device, an activity calculation system, and a control method and a control program of a mobile device, which are capable of calculating an activity factor indicating an activity amount.

According to the present disclosure, it is possible to calculate an activity factor indicating an activity amount.

Figure 1:
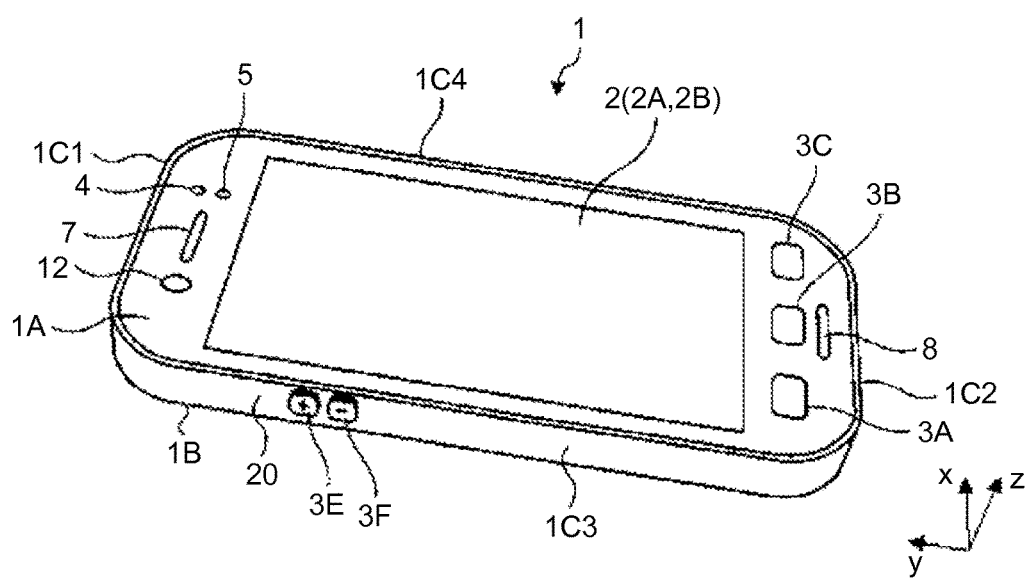
FIG. 1 is a schematic external appearance diagram illustrating an external appearance of a smartphone according to an embodiment of some embodiments.
Figure 2:
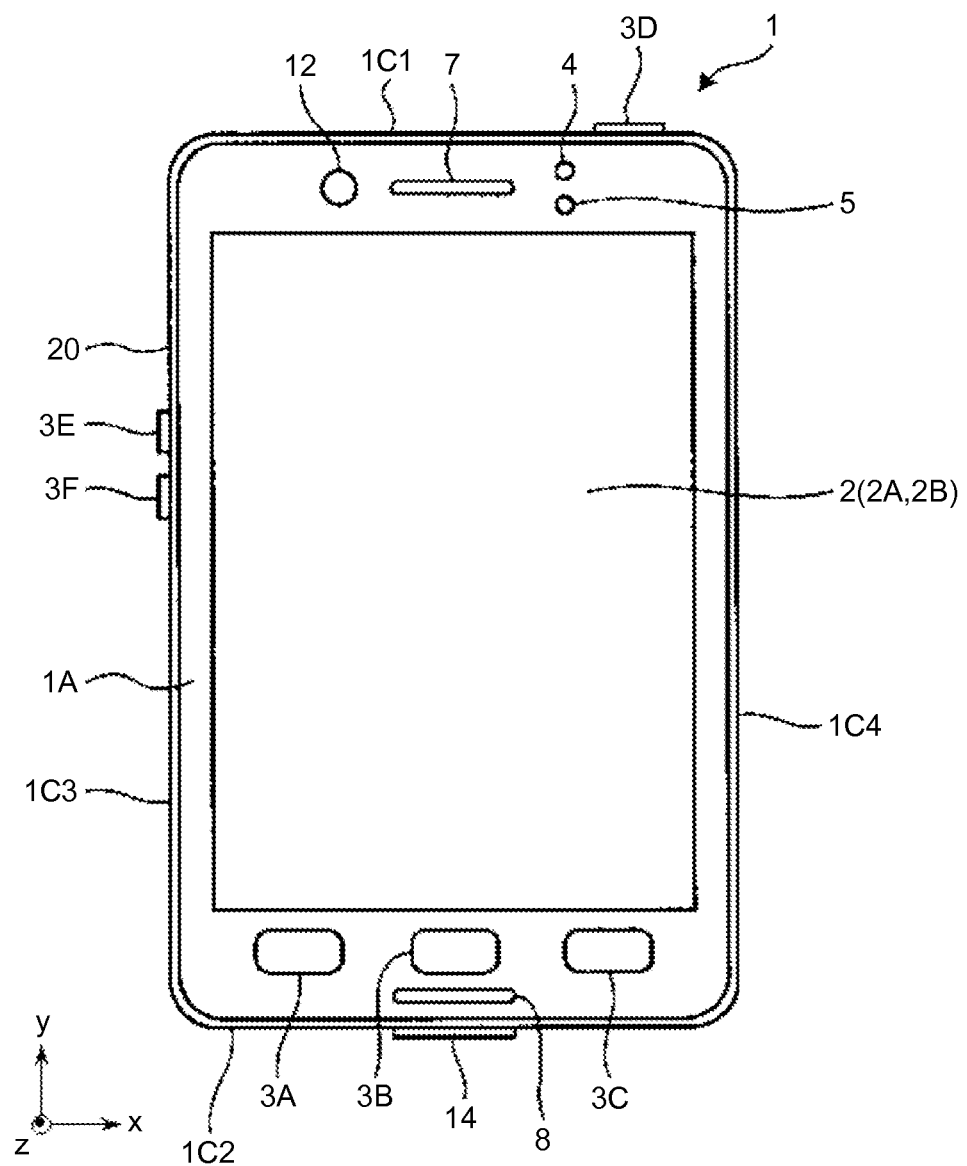
FIG. 2 is a schematic front view illustrating an external appearance of a smartphone according to an embodiment of some embodiments.
Figure 3:
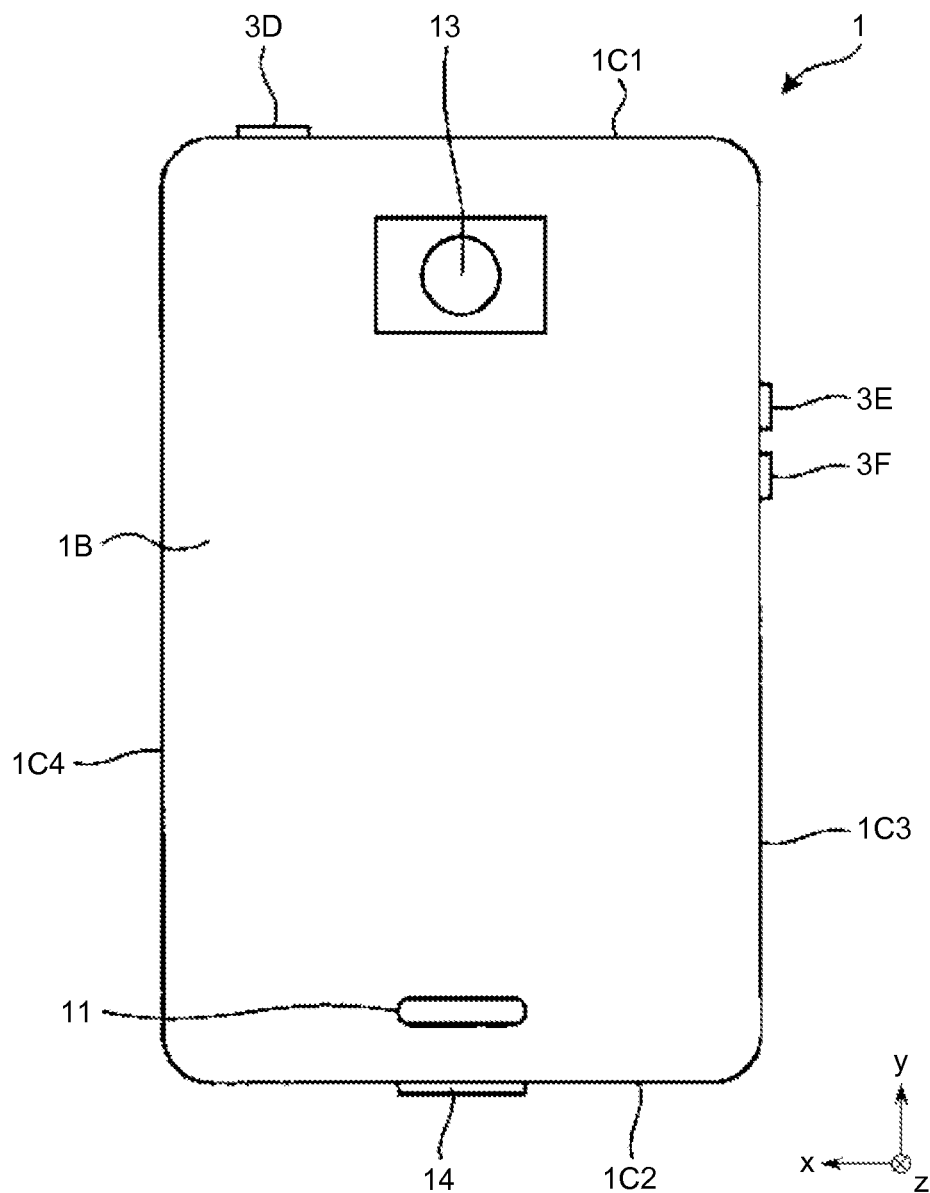
FIG. 3 is a schematic back view illustrating an external appearance of a smartphone according to an embodiment of some embodiments.

An external appearance of a smartphone 1 according to one of embodiments will be described with reference to FIGS. 1 to 3. The smartphone 1 includes a housing 20 as illustrated in FIGS. 1 to 3. The housing 20 includes a front face 1A, a back face 1B, and side faces 1C1 to 1C4. The front face 1A is a front face of the housing 20. The back face 1B is a back face of the housing 20. The side faces 1C1 to 1C4 are side faces connecting the front face 1A with the back face 1B. In the following description, there are cases where the side faces 1C1 to 1C4 are referred to collectively as a "side face 1C" without specifying a specific face.

The smartphone 1 includes a touch screen display module 2, buttons 3A to 3C, an illuminance sensor 4, a proximity sensor 5, a receiver 7, a microphone 8, and a camera 12 on the front face 1A. The smartphone 1 includes a camera 13 on the back face 1B. The smartphone 1 includes buttons 3D to 3F and a connector 14 on the side face 1C. In the following description, there are cases where the buttons 3A to 3F are referred to collectively as a "button 3" without specifying a certain button.

The touch screen display module 2 includes a display 2A and a touch screen 2B. The display 2A is equipped with a display device such as a liquid crystal display (LCD), an organic electro-luminescence (EL) panel, or an inorganic EL panel. The display 2A can display a text, an image, a symbol, or a diagram.

The touch screen 2B can detect, for example, a contact of a finger or a stylus pen with the touch screen 2B. The touch screen 2B can detect a position at which a plurality of fingers, a plurality of stylus pens, or the like contact with the touch screen 2B.

A detection method of the touch screen 2B may be an arbitrary method such as a capacitive method, a resistive method, a surface acoustic wave (SAW) (or an ultrasonic method), an infrared method, an electromagnetic induction method, or a load detection method. In the capacitive method, it is possible to detect a contact or an approach of a finger, a stylus pen, or the like.

Hereinafter, in order to simplify a description, there are cases where a finger, a stylus pen, and the like whose contact is detected through the touch screen 2B are referred to simply as a "finger."

The smartphone 1 can determine a type of gesture based on a contact detected by the touch screen 2B, a position at which a contact is detected, a period of time in which a contact is detected, and a temporal change of a position at which a contact is performed. A gesture is an operation performed on the touch screen display module 2. Examples of the gesture determined by the smartphone 1 include, but are not limited to, a touch, a long touch, a release, a swipe, a tap, a double tap, a long tap, a drag, a flick, a pinch-in, and a pinch-out.

The "touch" is a gesture in which the finger touches the touch screen 2B. The smartphone 1 can determine a gesture in which the finger contacts with the touch screen 2B as the touch. The "long touch" is a gesture in which the finger touches the touch screen 2B during a predetermined period of time or more. The smartphone 1 can determine a gesture in which the finger contacts with the touch screen 2B during a predetermined period of time or more as the long touch. A multi-touch is a gesture in which a plurality of fingers touch the touch screen 2B. The smartphone 1 can determine a gesture in which a plurality of fingers contact with the touch screen 2B as the touch. The "release" is a gesture in which the finger is separated from the touch screen 2B. The smartphone 1 can determine a gesture in which the finger is separated from the touch screen 2B as the release.

The "tap" is a gesture that the release is performed subsequently to the touch. The smartphone 1 can determine a gesture in which the release is performed subsequently to the touch as the tap. The "double tap" is a gesture in which the gesture in which the release is performed subsequently to the touch is consecutively performed twice. The smartphone 1 can determine a gesture in which the gesture in which the release is performed subsequently to the touch is consecutively performed twice as the double tap. The "long tap" is a gesture in which the release is performed subsequently to the long touch. The smartphone 1 can determine a gesture in which the release is performed subsequently to the long touch as the long tap. A multi-tap is a gesture in which the release is performed subsequently to the multi-touch. The smartphone 1 can determine a gesture in which the release is performed subsequently to the multi-touch as the multi-tap.

The "swipe" is a gesture in which the finger moves while contacting with the touch screen display module 2. The smartphone 1 can determine a gesture in which the finger moves while contacting with the touch screen display module 2 as the swipe. The "drag" is a gesture in which the swipe is performed starting from a region on which a movable object is being displayed. The smartphone 1 can determine a gesture in which the swipe is performed starting from a region on which a movable object is being displayed as the drag.

The "flick" is a gesture in which the release is performed while moving the finger in one direction at a high speed subsequently to the touch. The smartphone 1 can determine a gesture in which the release is performed while moving the finger in one direction at a high speed subsequently to the touch as the flick. Examples of the flick include, but are not limited to, an upward flick in which the finger moves in an upward direction of the screen, a downward flick in which the finger moves in a downward direction of the screen, a right flick in which the finger moves in a right direction of the screen, and a leftward flick in which the finger moves in a left direction of the screen.

The "pinch-in" is a gesture in which a plurality of fingers swipe in an approaching direction. The smartphone 1 can determine a gesture in which a plurality of fingers swipe in an approaching direction as the pinch-in. The "pinch-out" is a gesture in which a plurality of fingers swipe in a separating direction. The smartphone 1 can determine a gesture in which a plurality of fingers swipe in a separating direction as the pinch-out.

The smartphone 1 can perform the operation according to the gesture determined through the touch screen 2B. Since the operation is performed based on the gesture, operability in which the user can use the smartphone 1 intuitively and easily is implemented in the smartphone 1. An operation performed according to a determined gesture by the smartphone 1 differs according to a screen displayed on the touch screen display module 2.

Figure 4:
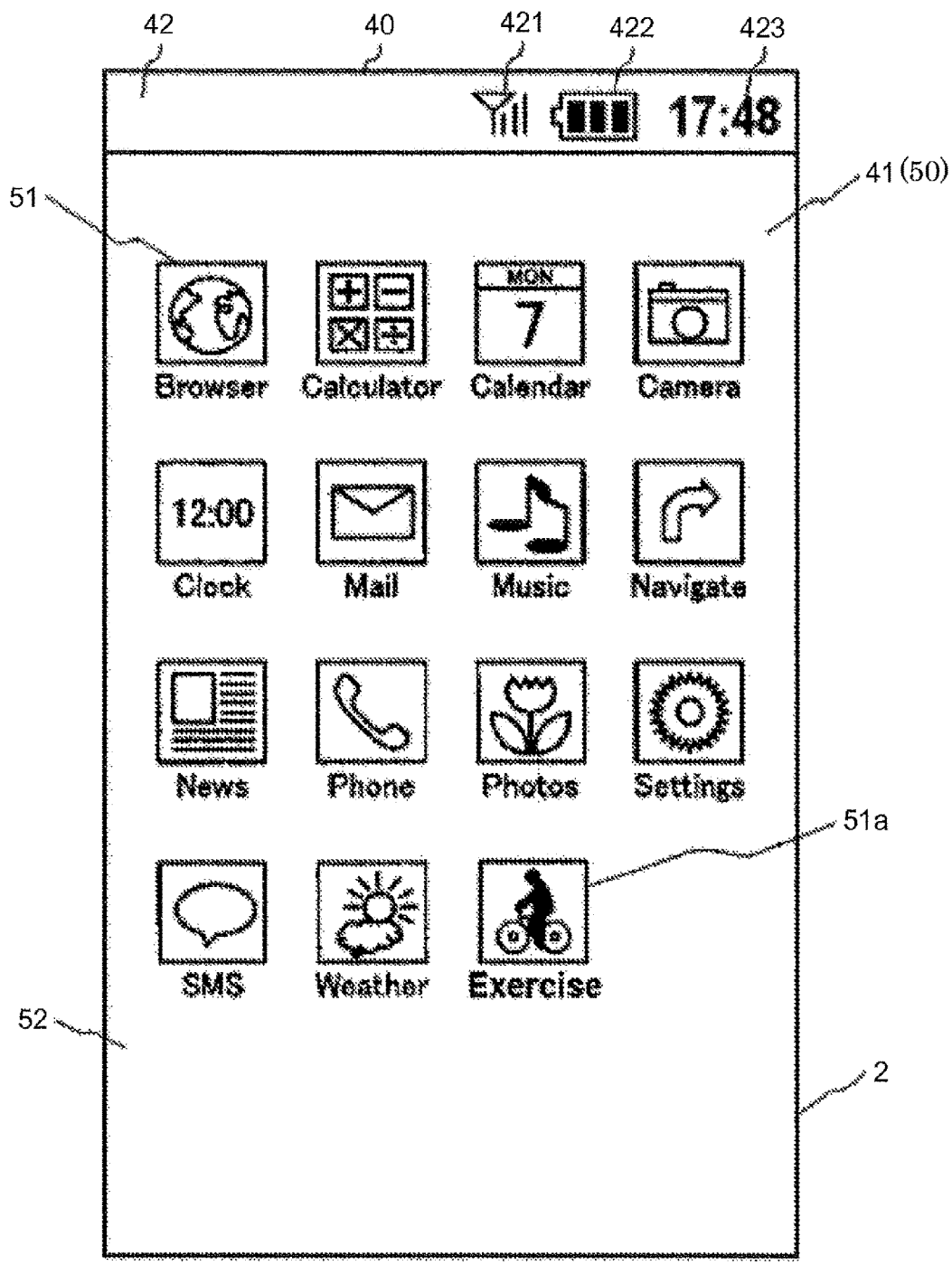
FIG. 4 is a diagram illustrating an exemplary home screen of some embodiments.

An exemplary screen displayed on the display 2A will be described with reference to FIG. 4. FIG. 4 illustrates an exemplary home screen. The home screen is also referred to as a "desktop," a "launcher," or an "idle screen." The home screen can be displayed on the display 2A. The home screen is a screen in which the user can select an application to be executed among applications installed in the smartphone 1. The smartphone 1 can execute an application selected on the home screen on the foreground. A screen of the application executed on the foreground can be displayed on a display region 40 of the display 2A.

In the smartphone 1, an icon may be arranged on the home screen. A home screen 50 illustrated in FIG. 4 can be displayed on a first region 41 of the display region of the display 2A. A plurality of icons 51 can be arranged on the home screen 50. The icons 51 can be associated with the applications installed in the smartphone 1 in advance. Upon detecting the gesture on the icon 51, the smartphone 1 can execute the application associated with the icon 51.

For example, upon detecting the tap on the icon 51 associated with a mail application, the smartphone 1 can execute the mail application.

For example, when the click on the button 3B is detected in a state in which the mail application is executed on the foreground, the smartphone 1 can display the home screen 50 on the first region 41 of the display 2A, and can execute the mail application on the background. Further, when the tap on the icon 51 associated with a browser application is detected, the smartphone 1 can execute the browser application on the foreground. The application executed on the background can be suspended or finished according to an execution state of the corresponding application or another application.

The icon 51 includes an image and a character string. The icon 51 may include a symbol or a diagram instead of an image. The icon 51 may include neither an image nor a character string. The icons 51 may be arranged according to a predetermined rule. A wallpaper 52 can be displayed on the back of the icon 51. The wallpaper is also called a photo screen or a back screen. The smartphone 1 can use an arbitrary image as the wallpaper 52. An arbitrary image may be decided as the wallpaper 52, for example, according to a setting performed by the user.

The smartphone 1 may increase the number of home screens. For example, the smartphone 1 may decide the number of home screens according to a setting performed by the user. Even when there are a plurality of home screens, the smartphone 1 can cause a selected home screen to be displayed on the display 2A. The smartphone 1 can display one or more locators on the home screen. The number of symbols of the locator is equal to the number of home screens. The symbol of the locator can indicate the position of the home screen that is currently being displayed. A symbol corresponding to the home screen that is currently being displayed can be displayed in a different form from the other symbols.

Upon detecting the gesture while the home screen is being displayed, the smartphone 1 can switch the home screen displayed on the display 2A. For example, upon detecting the right flick, the smartphone 1 can switch the home screen displayed on the display 2A to the next home screen on the left. For example, upon detecting the left flick, the smartphone 1 can switch the home screen displayed on the display 2A to the next home screen on the right. When the home screen is changed, the smartphone 1 can update a display of the locator according to the position of the changed home screen.

A second region 42 can be disposed on the top of the display region 40 of the display 2A. A remaining level mark 422 indicating a remaining battery level, a radio level mark 421 indicating field strength of a radio wave for communication, and a current time 423 can be displayed on the second region 42. The smartphone 1 may display a time, weather information, an application being executed, a type of communication system, a phone call status, a device mode, an event occurring in a device, or the like on the second region 42. The second region 42 can be used to given various kinds of notifications to the user. The second region 42 may be disposed on a screen other than the home screen 50. The position at which the second region 42 can be disposed is not limited to the top of the display 2A.

A vertical direction of the home screen 50 will be described. The vertical direction of the home screen 50 is a direction based on a vertical direction of a text or an image displayed on the display 2A. Thus, when the home screen 50 is displayed in a longitudinal direction, a side of the home screen 50 close to the second region 42 in the longitudinal direction of the touch screen display module 2 is an upper side of the home screen 50, and a side of the home screen 50 far from the second region 42 is a lower side of the home screen 50. A side of the second region 42 at which the current time 423 can be displayed is a right side of the home screen 50, and a side of the second region 42 at which the current time 423 is not displayed is a left side of the home screen 50.

The home screen 50 illustrated in FIG. 4 is an example, and forms of various kinds of elements, an arrangement of various kinds of elements, the number of home screens 50, and various kinds of operation methods in the home screen 50 may be different from those described above.

Figure 5:
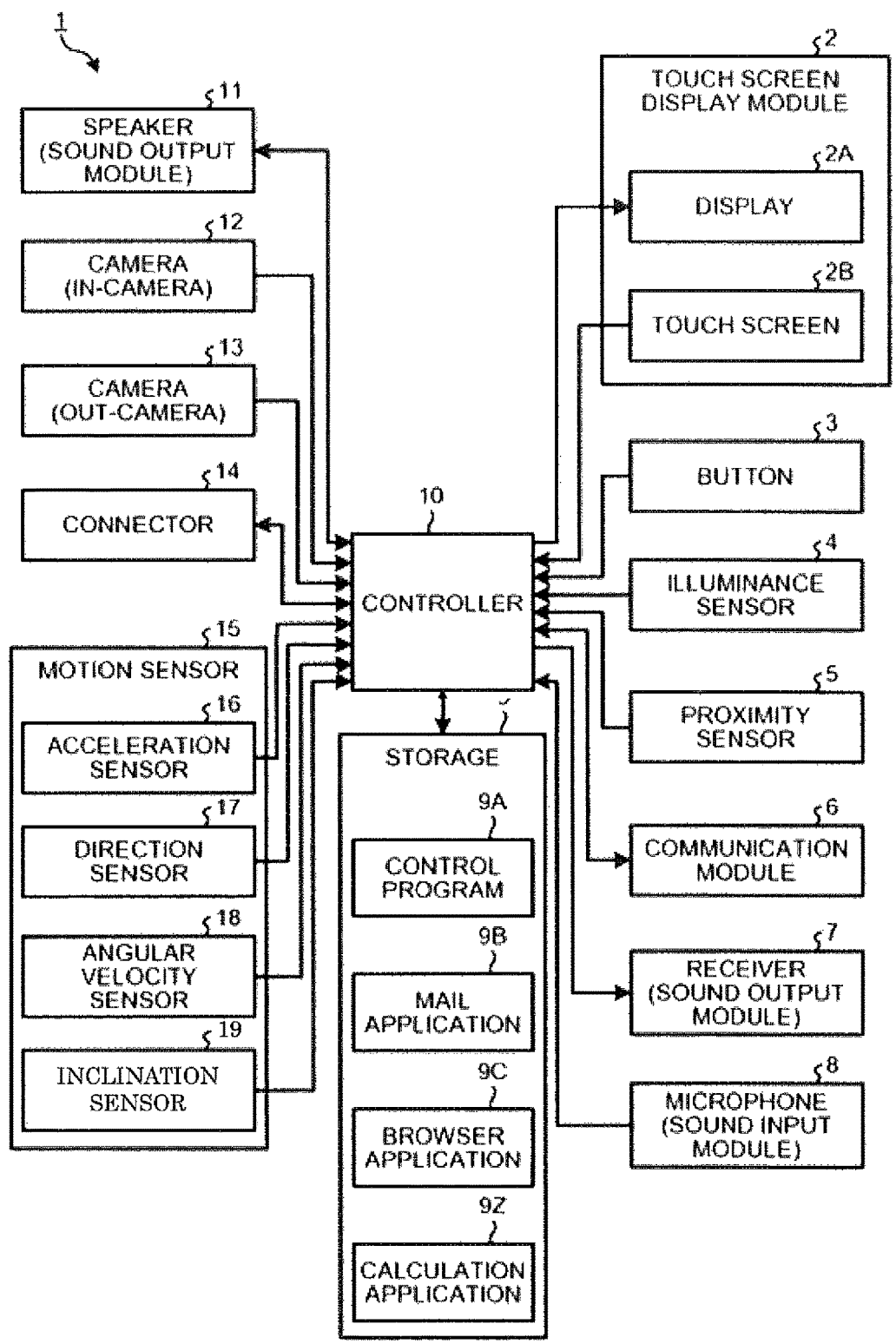
FIG. 5 is a schematic block diagram illustrating functions of a smartphone according to an embodiment of some embodiments.

FIG. 5 is a block diagram illustrating a configuration of the smartphone 1. The smartphone 1 include the touch screen display module 2, the button 3, the illuminance sensor 4, the proximity sensor 5, a communication module 6, the receiver 7, the microphone 8, a storage 9, a controller 10, the cameras 12 and 13, the connector 14, and a motion sensor 15.

The touch screen display module 2 includes the display 2A and the touch screen 2B as described above. The display 2A can display a text, an image, a symbol, a diagram, or the like. The touch screen 2B can detect a contact on a reception region as an input. In other words, the touch screen 2B can detect a contact. The controller 10 can detect a gesture on the smartphone 1. The controller 10 can detect an operation (gesture) on the touch screen 2B (the touch screen display module 2) in collaboration with the touch screen 2B. The controller 10 can detect an operation (gesture) on the display 2A (the touch screen display module 2) in collaboration with the touch screen 2B.

The button 3 may be operated by the user. The button 3 includes the buttons 3A to 3F. The controller 10 can detect an operation on the button in collaboration with the button 3. Examples of the operation on the button include, but are not limited to, a click, a double click, a push, a long push, and a multi-push.

The buttons 3A to 3C are, for example, a home button, a back button, and a menu button. In an embodiment, touch sensor type buttons are employed as the buttons 3A to 3C. The button 3D is, for example, a power on/off button of the smartphone 1. The button 3D may function as a sleep/wake-up button as well. The buttons 3E and 3F are, for example, volume buttons.

The illuminance sensor 4 can detect illuminance. For example, the illuminance can indicate intensity, brightness, or luminance of light. For example, the illuminance sensor 4 can be used to adjust luminance of the display 2A. The proximity sensor 5 can detect the presence of a nearby physical body in a non-contact manner. For example, the proximity sensor 5 can detect that the touch screen display module 2 has gotten closer to a face.

The communication module 6 can perform wireless communication. A communication scheme performed by the communication module 6 is a wireless communication standard. As the wireless communication standard, there are cellular communication standards such as 2G, 3G, and 4G communication standards, for example. An example of the cellular communication standard include, but are not limited to, long term evolution (LTE) standard, W-CDMA (a registered trademark) standard, CDMA2000 standard, PDC standard, GSM (a registered trademark) standard, and personal handy-phone system (PHS) standard. Examples of the wireless communication standard include, but are not limited to, worldwide interoperability for microwave access (WiMAX) standard, IEEE802.11 standard, BLUETOOTH (a registered trademark) standard, IrDA standard, and NFC standard. The communication module 6 may support one or more communication standards.

The receiver 7 can output a sound signal transmitted from the controller 10 as a sound. The microphone 8 can convert a voice of the user or the like into a voice signal, and can transmit the voice signal to the controller 10. The smartphone 1 may further include a speaker 11 in addition to the receiver 7. The smartphone 1 may further include a speaker instead of the receiver 7.

The storage 9 can store a program and data. The storage 9 can be also used as a work region that temporarily can store a processing result of the controller 10. The storage 9 may include an arbitrary storage device such as a semiconductor memory device or a magnetic storage device. The storage 9 may include a plurality of types of storage devices. The storage 9 may include a combination of a portable storage medium such as a memory card and a storage medium reading device.

Examples of a program stored in the storage 9 include an application executed on the foreground or the background and a control program that supports an operation of an application. For example, the application can cause a predetermined screen to be displayed on the display 2A and can cause the controller 10 to execute a process according to a gesture detected through the touch screen 2B. The control program is, for example, an OS. The application and the control program may be installed in the storage 9 through a wireless communication performed by the communication module 6 or a storage medium.

The storage 9 can store, for example, a control program 9A, a mail application 9B, a browser application 9C, and a calculation application 9Z that calculates an activity factor indicating an activity amount. The mail application 9B can provide an e-mail function of composing, transmitting, receiving, and displaying an e-mail. The browser application 9C can provide a web browsing function of displaying a web page. The calculation application 9Z can provide a function of calculating an activity factor indicating an activity amount using a motion on the smartphone 1 as a motion of the user.

The control program 9A can provide a function related to various kinds of control for operating the smartphone 1. The control program 9A can control, for example, the communication module 6, the receiver 7, the microphone 8, and the like such that a phone call is implemented. There are cases where the function provided by the control program 9A can be used in combination with a function provided by another program such as the mail application 9B.

The controller 10 is, for example, a central processing unit (CPU). The operational circuit may be an integrated circuit (IC) such as a system-on-a-chip (SoC) in which another component such as the communication module 6 are integrated. The controller 10 may be configured such that a plurality of ICs are combined. The controller 10 integrally can control the operation of the smartphone 1 such that various kinds of functions are implemented.

Specifically, the controller 10 can execute a command included in the program stored in the storage 9 with reference to data stored in the storage 9 as necessary, and can control the display 2A, the communication module 6, the motion sensor 15, and the like such that various kinds of functions are implemented. The controller 10 can execute a command included in the calculation application 9Z stored in the storage 9, and can implement various kinds of functions. The controller 10 may change control according to detection results of various kinds of detecting modules such as the touch screen 2B, the button 3, and the motion sensor 15.

The camera 12 is an in-camera that images a physical body facing the front face 1A. The camera 13 is an out-camera that images a physical body facing the back face 1B.

The connector 14 is a terminal to which another device is connected. The connector 14 of an embodiment also can function as a communication module that can enable the smartphone 1 to communicate with another device through a connector connected to a corresponding terminal. The connector 14 may be a general-purpose terminal such as a universal serial bus (USB) terminal, a high-definition multimedia interface (HDMI (a registered trademark)) terminal, a mobile high-definition link (MHL) terminal, a light peak terminal, a THUNDERBOLT (a registered trademark)) terminal, a local area network (LAN) connector, or an earphone microphone connector. The connector 14 may be a dedicated terminal such as a dock connector. Examples of the device connected to the connector 14 include, but are not limited to, a charger, an external storage, a speaker, a communication device, and an information processing device.

The motion sensor 15 can detect a motion factor. The motion factor can be mainly processed as a control factor of the smartphone 1 serving as an own device through the controller 10. The controller 10 can mainly process the motion factor detected by the motion sensor 15 as the control factor indicating a given state of the own device. The motion sensor 15 of an embodiment includes an acceleration sensor 16, a direction sensor 17, an angular velocity sensor 18, and an inclination sensor 19.

The acceleration sensor 16 can detect acceleration working on the smartphone 1. The acceleration sensor 16 can output the detected acceleration. For example, when an acceleration direction is output as the motion factor, the controller 10 can use the control factor in which the direction in which the smartphone 1 moves is reflected for processing. For example, when an acceleration magnitude is output, the controller 10 can use the control factor in which the direction in which the smartphone 1 moves is reflected for processing. In an embodiment, a sensor capable of detecting acceleration in three axis directions can be employed as the acceleration sensor 16. The three axis directions detected by the acceleration sensor 16 of an embodiment are substantially orthogonal to one another. An x direction, a y direction, and a z direction illustrated in FIGS. 1 to 3 correspond to the three axis directions of the acceleration sensor 16.

The direction sensor 17 can detect a geomagnetism orientation. The direction sensor 17 can output the detected geomagnetism orientation. For example, when the geomagnetism orientation is output as the motion factor, the controller 10 can use the control factor in which a direction in which the smartphone 1 faces is reflected for processing. For example, when a change in the geomagnetism orientation is output as the motion factor, the controller 10 can use the control factor in which the change in the direction in which the smartphone 1 faces is reflected for processing.

The angular velocity sensor 18 can detect an angular velocity of the smartphone 1. The angular velocity sensor 18 can output the detected angular velocity. For example, when the presence or absence of the angular velocity is output as the motion factor, the controller 10 can use the control factor in which rotation of the smartphone 1 is reflected for processing. For example, when an orientation of the angular velocity is output as the motion factor, the controller 10 can use the control factor in which the rotation direction of the smartphone 1 is reflected for processing. In an embodiment, a sensor capable of detecting the angular velocity in the three axis directions can be employed as the angular velocity sensor 18. The x direction, y direction, z direction illustrated in FIGS. 1 to 3 correspond to the three axis direction of the angular velocity sensor 18. The inclination sensor 19 can detect an inclination of the smartphone with respect to the gravity direction.

The inclination sensor 19 can detect an inclination of the smartphone 1 with respect to the gravity direction. The inclination sensor 19 can output the detected inclination. For example, when the inclination with respect to the gravity direction is output as the motion factor, the controller 10 can use the control factor in which the inclination of the smartphone 1 is reflected for processing.

The outputs of the acceleration sensor 16, the direction sensor 17, the angular velocity sensor 18, and the inclination sensor 19 of the motion sensor 15, that is, outputs of a plurality of sensors can be combined and used. As the outputs of the motion sensor 15 are combined and processed, the controller 10 can execute a process in which a motion in the smartphone 1 serving as the own device is reflected at a high speed.

The smartphone 1 can process the motion factor detected by the motion sensor 15 as the control factor in which at least one of an attitude change, a position change, and a direction change is reflected. The process using the control factor can be executed by the controller 10. In an embodiment, a change in the inclination in the three axis directions of the smartphone 1 with respect to the gravity direction can be used as the attitude change.

As an example in which the motion factor can be used as the control factor of the attitude change, there is a process of changing a display direction of the screen. The smartphone 1 can compare the x axis direction with the y axis direction, and can change the display direction of the screen so that the screen can be displayed along the axis direction closer to the gravity direction. When the display direction of the screen is changed, the smartphone 1 can process the motion factor as the control factor, and can determine a physical orientation of the screen.

As an example in which the motion factor can be used as the control factor of the position change, there is a process of updating the position of the smartphone 1 in a place where a GPS signal is hardly received. When the position is updated, the smartphone 1 can process the motion factor as the control factor, and can calculate the moving distance. This process is not limited to the place where the GPS signal is hardly received, and it is possible to process together with the GPS signal in order to increase the position accuracy.

As an example in which the motion factor can be used as the control factor of the direction change, there is a process of updating the direction of the smartphone 1 in a place where the geomagnetism is hardly detected. When the direction change is updated, the smartphone 1 can process the motion factor as the control factor, and can calculate an amount of axial rotation. This process is not limited to the place where the geomagnetism is hardly detected, and it is also possible to process together with a geomagnetism detection signal in order to increase the direction accuracy.

In an embodiment, the motion factor output from the motion sensor 15 may undergo an operation performed by the controller 10 and be used for analysis of motion of the user. The controller 10 may analyze the motion of the user and determine a movement method such as whether the user is walking, the user is running, the user is riding a bicycle, the user is riding in an automobile, the user is riding a motorcycle, or the user is on an airplane. When the user is riding in an automobile, there are a case where the user is driving and a case where another person is driving. The determination of the movement method of the user based on the motion factor may be executed at the same time when the controller 10 processes the motion factor as the control factor or may be executed after a mode is switched.

The sensors in which three directions are orthogonal to one another can be employed as the acceleration sensor 16 and the angular velocity sensor 18 of an embodiment, but the three directions may not be orthogonal to one another. In the acceleration sensor and the angular velocity sensor in which the three directions are not orthogonal, it is possible to calculate the acceleration and the angular velocity in three orthogonal directions through an operation. The directions that are used as a reference by the acceleration sensor and the angular velocity sensor may be different from each other.

Some or all of programs stored in the storage 9 in FIG. may be downloaded from another device through wireless communication performed by the communication module 6. Some or all of programs stored in the storage 9 in FIG. 5 may be stored in a storage medium that is readable by a read device and included in the storage 9. Some or all of programs stored in the storage 9 in FIG. 5 may be stored in a storage medium that is readable by a read device connected to the connector 14 such as a flash memory, a hard disc drive (HDD), a compact disc (CD), a digital versatile disc (DVD), or a BLU-RAY disc (a registered trademark) (BD).

The configuration of the smartphone 1 illustrated in FIG. 5 is an example and may be appropriately modified within the scope not departing from the gist of the present disclosure. For example, the number and types of buttons 3 are not limited to those in an example of FIG. 5. The smartphone 1 may be equipped with buttons a ten-key arrangement or a QWERTY arrangement as buttons for an operation related to the screen instead of the buttons 3A to 3C. The smartphone 1 may be equipped with one button for an operation related to the screen or may be equipped with no button. In an example illustrated in FIG. 5, the smartphone 1 is equipped with two cameras, but the smartphone 1 may be equipped with one camera or may be equipped with no camera. The illuminance sensor 4 and the proximity sensor 5 may be configured with one sensor. In an example illustrated in FIG. 5, the smartphone 1 is equipped with the three types of sensors for detecting a position and an attitude, but the smartphone 1 may not be equipped with some of the sensors and may be equipped with another type of sensor for detecting a position and an attitude.

Figure 6:
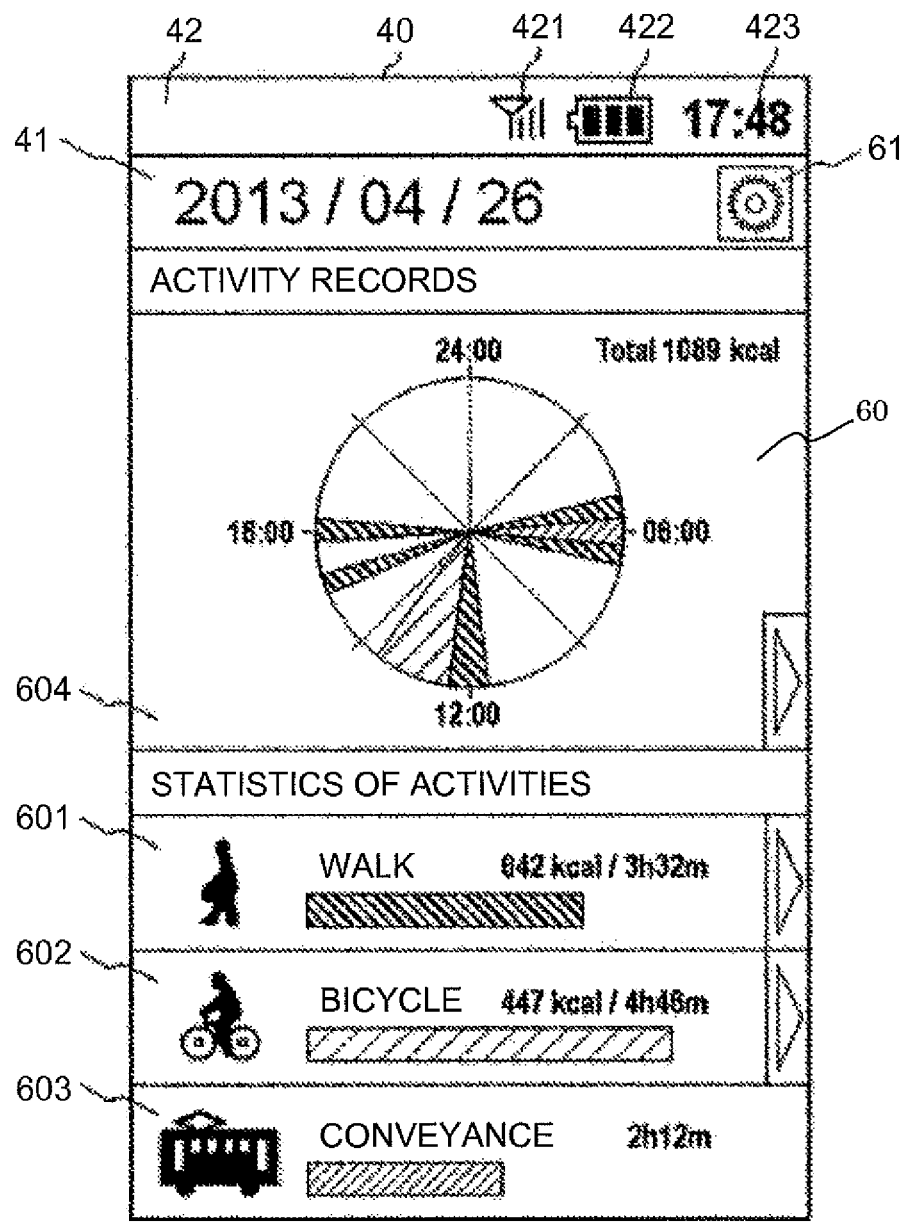
FIG. 6 is a diagram illustrating an exemplary display screen of a smartphone according to an embodiment of some embodiments.

FIG. 6 illustrates a screen example in which the smartphone 1 can display the activity factor of the user according to the calculation application 9Z. An activity factor display screen 60 illustrated in FIG. 6 can be displayed on the display 2A, for example, by tapping an icon 51a labeled with "Exercise" among the icons 51 illustrated in FIG. 4.

In the display screen 60 illustrated in FIG. 6, the motion of the user can be analyzed based on the motion factor detected by the motion sensor 15, and the movement method of the user can be displayed. In the display screen 60 illustrated in FIG. 6, activity records of the respective movement methods can be displayed on regions 601 to 603. A walk indicating a case where the user moves by walk and running can be displayed on the region 601. A bicycle indicating a case where the user moves by bicycle can be displayed on the region 602. A conveyance indicating a case where the user moves by an automobile, a motorcycle, or an airplane can be displayed on the region 603. The display of the movement methods are not limited to the classification methods employed in FIG. 6, and walking and running may be differently displayed, and an automobile, a motorcycle, and an airplane may be differently displayed.

In the region 601, an icon and a character string indicating that the movement method is a walk, a character string indicating a total time in which the user has moved by walk, a flag indicating a moving time visually, and a calorie consumed by the user by walk can be displayed. In the region 602, an icon and a character string indicating that the movement method is a bicycle, a character string indicating a total time in which the user has moved by bicycle, a flag indicating a moving time visually, and a calorie consumed by the user by walk can be displayed. In the region 603, an icon and a character string indicating that the movement method is a conveyance, a character string indicating a total time in which the user has moved by conveyance, and a flag indicating a moving time visually can be displayed.

In an example illustrated in FIG. 6, a thermodynamic calorie (cal) can be employed as a "measurement of a calorie of a material eaten by humans or animals or a calorie consumed by metabolism by humans or animals" based on a Japanese measurement. A calorie measurement is not limited thereto, and a joule (J) based on a conference general des poids et mesures (CGPM) may be employed, and a calorie and a joule may be used together. Any of the matters displayed on the regions 601 to 603 may be omitted, and a new matter may be added. Examples of the matter that is added and displayed include, but are not limited to, a moving distance of each movement method, a fat combustion amount, an exercise, and the number of steps when the user has moved by walk. The "fat combustion amount" refers to an amount in which body fat is burned by body activities. The fat combustion amount is calculated from calorie consumption necessary to burn fat of one gram. The "exercise" is a unit indicating an amount of body activity. The exercise is an amount of exercise calculated by multiplying METs (which will be described later) by a body activity hour.

In the region 604, an activity record of one day of the user can be displayed. In the activity record of one day, a time at which a body activity was done can be displayed in association with a movement method when a body activity is done. In the smartphone 1, since the time and the movement method can be displayed in association with each other, the user can easily understand the activity record of one day visually.

In an example illustrated in FIG. 6, a calorie of each movement method that is an activity factor serving as an element indicating part of an activity amount of the user and a total calorie of one day can be displayed on the display 2A. The activity factor can be an element indicating part of a total activity amount of one day of the user, and can include the fat combustion amount, the "exercise," and the like in addition to the calorie. In FIG. 6, a calorie consumed by an activity of the user can be displayed for each movement method. Since a consumed calorie can be displayed for each movement method, the user can easily understand a result of his/her activity for each movement method through the smartphone 1. In an example illustrated in FIG. 6, a total calorie of one day consumed by the body activity of the user can be displayed. Since the consumed total calorie of one day can be displayed, the user can understand the total calorie indicating his/her body activity through the smartphone 1.

The calorie illustrated in FIG. 6 can be easily calculated based on intensity of the body activity of the user, a period of time of the body activity of the user, and a weight of the user. A simplified calculation formula is expressed by Formula 1:

$$\text{Energy consumption (kcal)} = \text{METs} \times \text{Body activity hour (h)} \times \text{Weight (kg)} \quad \text{(Formula 1)}$$

In an energy consumption calculation formula expressed by Formula 1, an element "METs" can be used. The MET can be a unit indicating the intensity of the body activity. The intensity of the body activity can differ according to a type of body activity. In an embodiment, the MET serving as the intensity of the body activity can be set for each movement method determined as a result of analyzing the motion of the user. In other words, in an embodiment, the MET can be used for calculation of the activity factor as a coefficient according to a type of motion factor. The MET functions as an operation factor that can be used for an operation of energy consumption serving as an activity factor indicating an activity amount. The MET can be indicated as the ratio with respect to the intensity of the body activity at rest. For example, a state in which the user is taking a rest on a seat can correspond to one MET, and a normal walk can correspond to three METs. In other words, it can mean that the intensity of the body activity of the normal walk is three times as high as the intensity of the body activity at rest.

In an energy consumption calculation formula expressed by Formula 1, an element a "body activity hour" can be used. The body activity hour can be a total time in which a body activity of a type corresponding to the METs used for a calculation among body activities of the user has been done. The body activity hour can function as an operation factor that can be used for an operation of energy consumption serving as an activity factor indicating an activity amount. The body activity hour can be a measured value based on a result of determining the motion factor detected by the motion sensor 15 through the controller 10. For example, numerical values indicating the body activity hour can be displayed on the regions 601 to 603 as the moving time.

In an energy consumption calculation formula expressed by Formula 1, an element "weight" can be used. The weight can be a weight of the user. The weight of the user can function as an operation factor that can be used for an operation of energy consumption serving as an activity factor indicating an activity amount. The weight of the user can be set as a setting item of the calculation application 9Z in advance. For example, in the calculation application 9Z, each item can be set, for example, by tapping an icon 61 illustrated in FIG. 6. Examples of the setting item of the calculation application 9Z include, but are not limited to, a date of birth, a height, a stride length, and a weight.

The date of birth can be a value indicating a date of birth of the user. The smartphone 1 can calculate an age of the user based on the date of birth. The calculated age of the user can be used in referring to various statistical data. A sex can be an item indicating a sex of the user. The smartphone 1 can refer to various statistical data according to the sex of the user.

The height can be a value indicating the height of the user. The smartphone 1 can calculate various items using the height of the user or can refer to various statistical data according to the height of the user. As an item calculated using the height of the user, for example, there is a body mass index (BMI). The BMI can be one of criteria used to determine obesity, which is advocated by the World Health Organization (WHO). The BMI is calculated by dividing a weight (kg) by the square of a height (m).

The stride length can be a value indicating the stride length of the user. The smartphone 1 can calculate a walking distance of the user using the stride length of the user. In an embodiment, a value of 45% of the height can be automatically input as a rough standard of the stride length. The stride length can be changed from the value input as the rough standard to an actually measured value.

The weight can be an element indicating the weight of the user. The smartphone 1 can calculate the energy consumption based on Formula 1 using the weight of the user. The smartphone 1 of an embodiment can acquire the weight of the user from the outside through the communication module 6. The smartphone 1 of an embodiment can acquire the weight of the user from the outside through the communication module 6, but the embodiments are not limited thereto. For example, the smartphone 1 may receive the weight of the user from the outside through the connector 14. The receiving of the weight of the user by the smartphone 1 can be controlled by the controller 10.

Upon receiving the weight of the user from the outside, the smartphone 1 can store the received weight in the storage 9 as the weight serving as the setting item of the calculation application 9Z. When the received weight of the user is stored, the smartphone 1 can store a reception date and time. The received weight of the user can be used for a calculation of energy consumption serving as an activity factor by the controller 10. Upon receiving the weight of the user, the smartphone 1 can calculate the body activity hour based on the motion factor after the reception date and time of the weight and the activity factor based on the received weight.

The activity factor can be calculated from the measured value based on the motion factor after the receiving using the received weight, and thus a more appropriate value can be calculated as the activity factor.

A control method of the smartphone 1 including the motion sensor 15 described using an example in which the received weight of the user can be used for a calculation of the energy consumption includes a step of receiving the weight of the user used for a calculation of an activity factor indicating an activity amount of motion detected by the motion sensor 15 and a step of calculating the energy consumption indicating the activity amount using the measured value based on the motion factor detected by the motion sensor 15 and the received weight of the user.

In the smartphone 1 of an embodiment, after a first weight received from the outside is stored in the storage 9, when a second weight is received from the outside, the second weight can be stored in the storage 9 as the weight serving as the setting item of the calculation application 9Z. At this time, the smartphone 1 preferably can store the first weight and the second weight separately. Since the first weight and the second weight are stored separately, the smartphone 1 can use the first weight for a calculation of a first activity factor based on a first motion factor after the first weight is received and use the second weight for a calculation of a second activity factor based on a second motion factor after the second weight is received. Since the first weight and the second weight are separately stored, the smartphone 1 can more accurately calculate the activity factor according to the period of time in which the motion factor has been measured.

In the smartphone 1 of an embodiment, when the weight of the user is received from the outside, a date and time at which the weight of the user is measured can be received together with the weight of the user. The smartphone 1 can use the received weight for a calculation of the activity factor based on the motion factor after the date and time at which the weight of the user is measured. Since the date and time at which the weight is measured can be received together with the weight of the user, the smartphone 1 can more accurately calculate the activity factor according to the period of time in which the motion factor has been measured. Since the date and time at which the weight can be measured is received together with the weight of the user, even when a plurality of weights of the user are simultaneously received, the smartphone 1 can more accurately calculate the activity factor according to the period of time in which the motion factor has been measured. Instead of the date and time at which the weight is measured, a date and time at which the weight of the user is stored in a server may be employed.

The smartphone 1 of an embodiment can transmit the calculated activity factor to the outside through the communication module 6. The smartphone 1 of an embodiment can transmit the calculated activity factor to the outside through the communication module 6, but the embodiments are not limited thereto. For example, the smartphone 1 may transmit the calculated activity factor to the outside through the connector 14. The transmitting of the activity factor by the smartphone 1 can be controlled by the controller 10.

An exemplary embodiment for carrying out the activity calculation system of the present disclosure will be described in detail with reference to the appended drawings. In the following description, a smartphone is described as an exemplary mobile device, and a weight scale is described as an exemplary measuring device.

Figure 7:
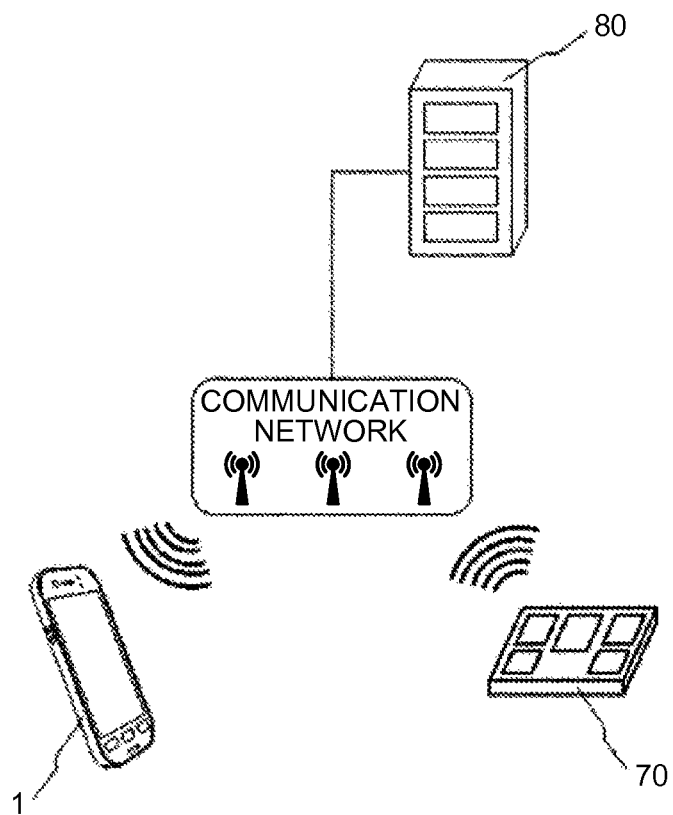
FIG. 7 is a conceptual diagram illustrating a schematic configuration of an activity calculation system according to an embodiment of some embodiments.
Figure 8:
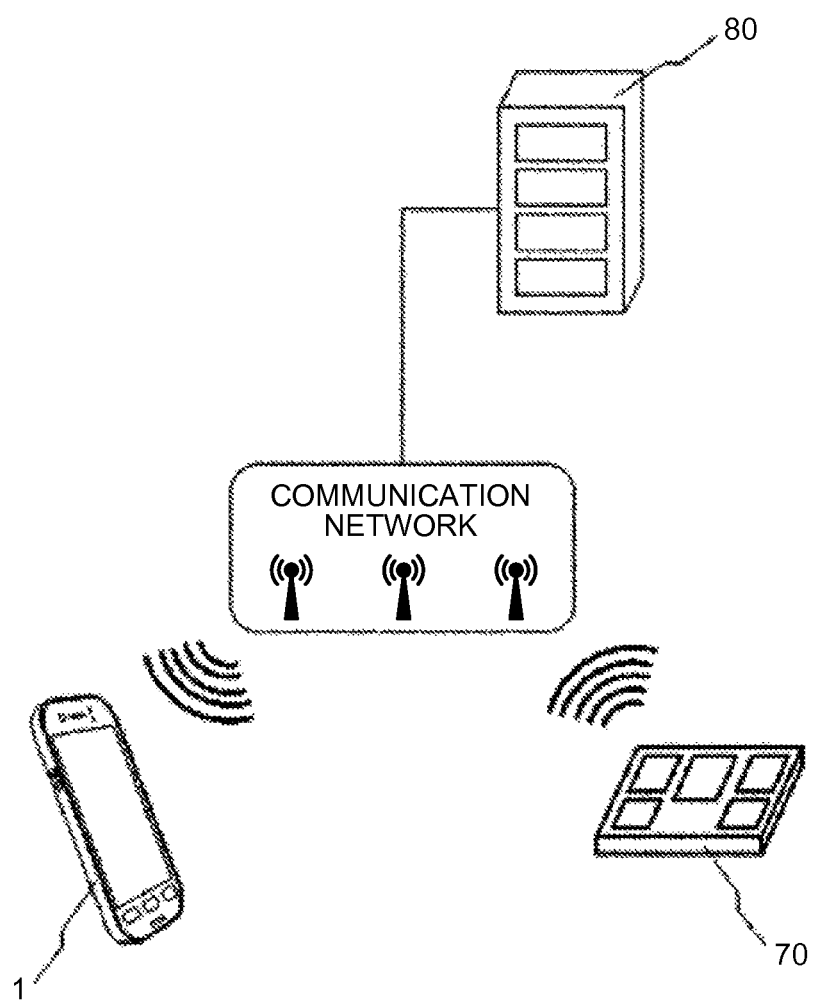
FIG. 8 is a conceptual diagram illustrating a schematic configuration of an activity calculation system according to an embodiment of some embodiments.

An activity calculation system of FIG. 7 according to an embodiment is configured to include a weight scale 70, a server 80, and a smartphone 1. Since the activity calculation system can be constructed by the measuring device, the mobile device, and the server as illustrated in FIG. 7, it is easy to collect information from a plurality of measuring devices as an operation factor. An activity calculation system of FIG. 8 according to an embodiment is configured to include a weight scale 70 and a smartphone 1. Since the activity calculation system can be constructed by the measuring device and the mobile device as illustrated in FIG. 8, it is possible to construct the system simply. Since the activity calculation system can be constructed by the measuring device and the mobile device as illustrated in FIG. 8, it is easy to cause an operation factor to be immediately updated in the mobile device. The smartphones 1 illustrated in FIGS. 7 and 8 have the same configuration as the smartphone illustrated in FIGS. 1 to 6.

Figure 9:
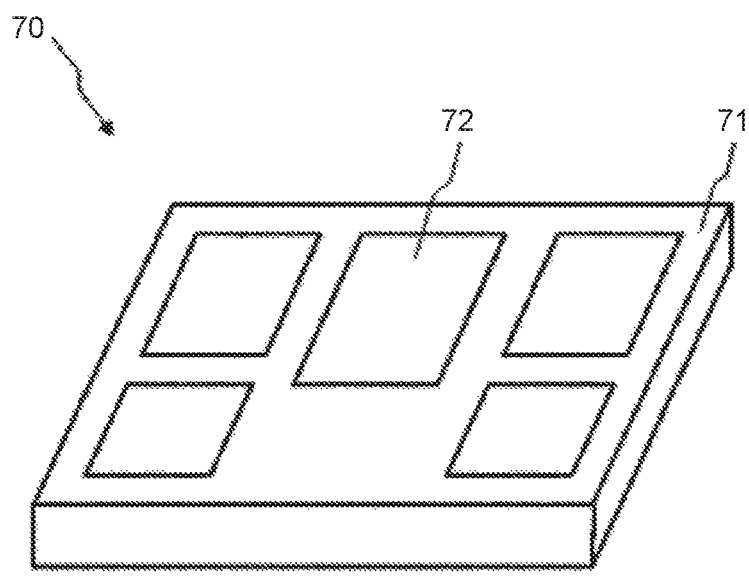
FIG. 9 is a schematic external appearance diagram illustrating an external appearance of a weight scale according to an embodiment of some embodiments.
Figure 10:
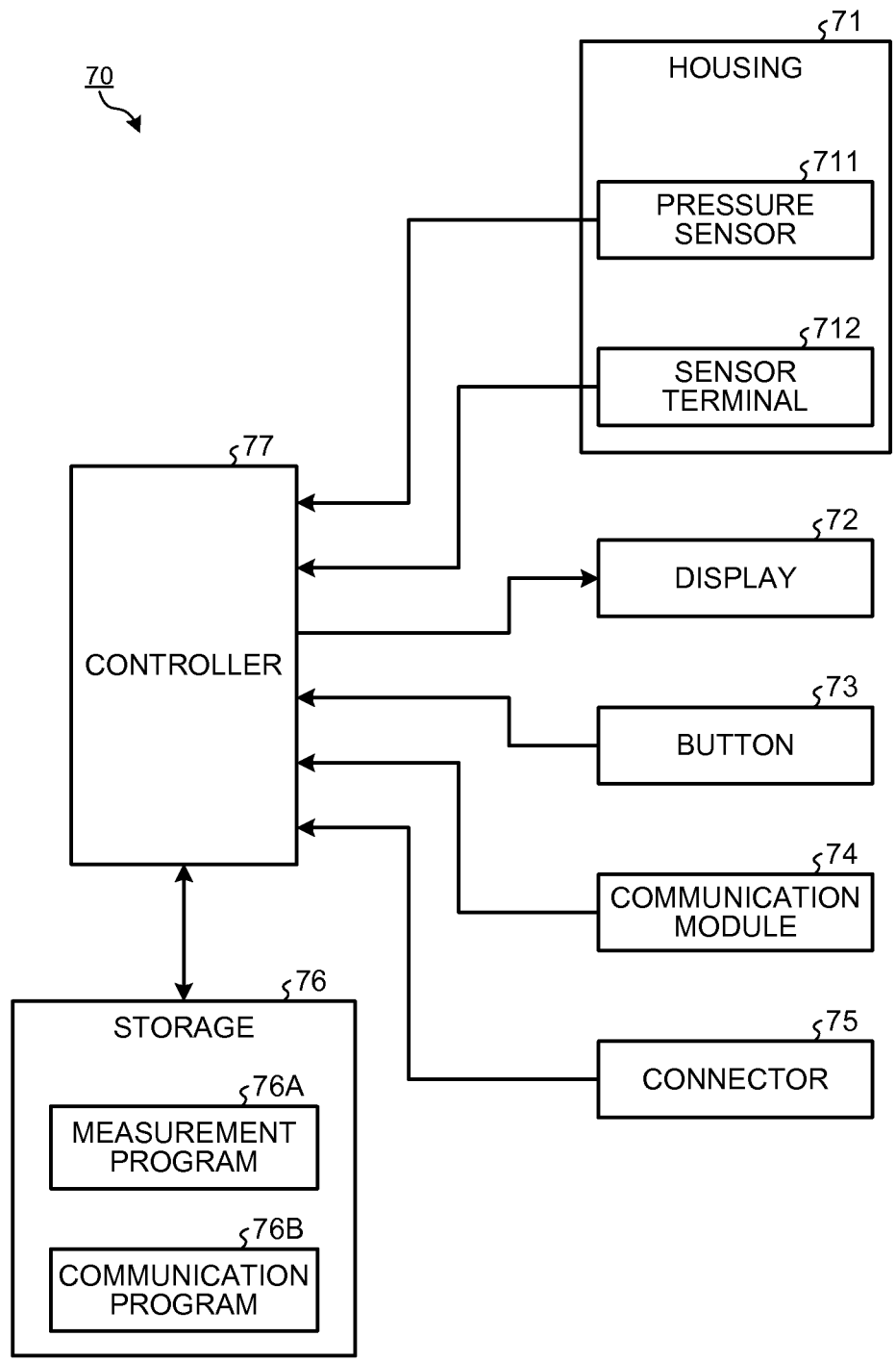
FIG. 10 is a schematic block diagram illustrating functions of a weight scale according to an embodiment of some embodiments.

FIG. 9 illustrates a schematic shape of the weight scale 70 serving as an exemplary measuring device. The weight scale 70 is configured to include a housing 71, a display 72, a button 73, a communication module 74, a connector 75, a storage 76, and a controller 77 as in a block configuration illustrated in FIG. 10.

The housing 71 can be a member functioning as a support base material of the weight scale 70. The housing 71 is configured to include a pressure sensor 711 and a sensor terminal 712.

The pressure sensor 711 can be a member that can detect the weight of the user as a load. The pressure sensor 711 can output the detected load to the controller 77, the pressure sensor 711 of an embodiment can function as a measuring module that measures an operation factor serving as body information of the user. A part of the pressure sensor 711 of an embodiment functions as a part of the shell of the housing 71.

The sensor terminal 712 can be a member that can detect electrical characteristics of the user. The sensor terminal 712 can flow a weak electrical current to the user. The sensor terminal 712 can output the electrical characteristics flowing to the user to the controller 77 as information for determining the body information of the user. The sensor terminal 712 of an embodiment can function as a measuring module that measures an operation factor serving as the body information of the user. The sensor terminal 712 of an embodiment can function as a part of the shell of the housing 71.

The display 72 can be a member serving as a user interface from the weight scale 70 to the user. The display 72 can display various information of the weight scale 70. For example, a measured weight, base metabolism, and the like can be displayed on the display 72.

The button 73 can be a member that receives an operation on the weight scale 70. The user can operate the weight scale 70 using the button 73.

The communication module 74 can be a member that transmits measurement information from the weight scale 70 to the outside. The communication module of an embodiment can transmit the measurement information and transmit a date and time at which the measurement information is obtained. As the date and time at which the measurement information is obtained are transmitted, the communication module 74 can more accurately transfer the body information of the user.

A communication scheme performed by the communication module 74 can be a wireless communication standard. As the wireless communication standard, there are cellular communication standards such as 2G, 3G, and 4G communication standards, for example. Examples of the cellular communication standard include, but are not limited to, LTE standard, W-CDMA (a registered trademark) standard, CDMA2000 standard, PDC standard, GSM (a registered trademark) standard, and PHS standard. Examples of the wireless communication standard include, but are not limited to, WiMAX standard, IEEE802.11 standard, BLUETOOTH (a registered trademark) standard, IrDA standard, and NFC standard. The communication module 74 may support one or more communication standards.

In examples of FIGS. 7 and 8, the weight scale 70 can communicate with the smartphone 1 via a communication network, but the embodiments are not limited thereto. The weight scale 70 may perform wireless communication with the smartphone 1 through the communication module 74 that supports any one of IEEE802.11, Bluetooth (a registered trademark), IrDA, NFC, and the like without intervention of a communication network.

The connector 75 can be a terminal to which another device is connected. The connector 75 of an embodiment also can function as a communication module that can enable the weight scale 70 to communicate with another device through a connector connected to a corresponding terminal. The connector 75 may be a general-purpose terminal such as a USB terminal, an HDMI (a registered trademark) terminal, an MHL terminal, a light peak terminal, a thunderbolt terminal, or an earphone microphone connector. The connector 75 may be a dedicated terminal such as a dock connector. Examples of the device connected to the connector 75 include, but are not limited to, a charger, an external storage, a speaker, a communication device, and an information processing device.

In an examples of FIGS. 7 and 8, the weight scale 70 can communicate with the smartphone 1 via a communication network, but the embodiments are not limited thereto. The weight scale 70 may preferentially perform wireless communication with the smartphone 1 through the connector 75 that is suitable for any one of USB, a LAN connector, an HDMI (a registered trademark) terminal, a MHL terminal, a light peak, a THUNDERBOLT terminal, and an earphone microphone cable without intervention of a communication network.

The storage 76 can store various programs such as a measurement program 76A and a communication program 76B. The measurement program 76A can provide a function of measuring the body information such as the weight of the user. In an embodiment, the operation factor used for a calculation of the activity factor can be measured by the measurement function provided by the measurement program 76A. The communication program 76B can provide a function of transmitting the measured body information of the user to another device. In an embodiment, the measured operation factor can be transmitted to the outside through the transmission function provided by the communication program 76B. In an example illustrated in FIG. 7, the operation factor can be transmitted to the server 80, and in an example illustrated in FIG. 8, the operation factor can be transmitted to the smartphone 1.

The controller 77 is, for example, a CPU. The controller 77 may be an IC such as an SoC in which another component such as the communication module 74 is integrated. The controller 77 may be configured such that a plurality of ICs are combined. The controller 77 integrally can control the operation of the weight scale 70 such that various kinds of functions are implemented.

Specifically, the controller 77 can execute a command included in the program stored in the storage 76 with reference to data stored in the storage 76 as necessary, and can control the pressure sensor 711, the sensor terminal 712, the display 72, the button 73, the communication module 74, the connector 75, and the like such that various kinds of functions are implemented. The controller 77 can execute a command included in the measurement program 76A stored in the storage 76, and implements various kinds of functions.

Figure 11:
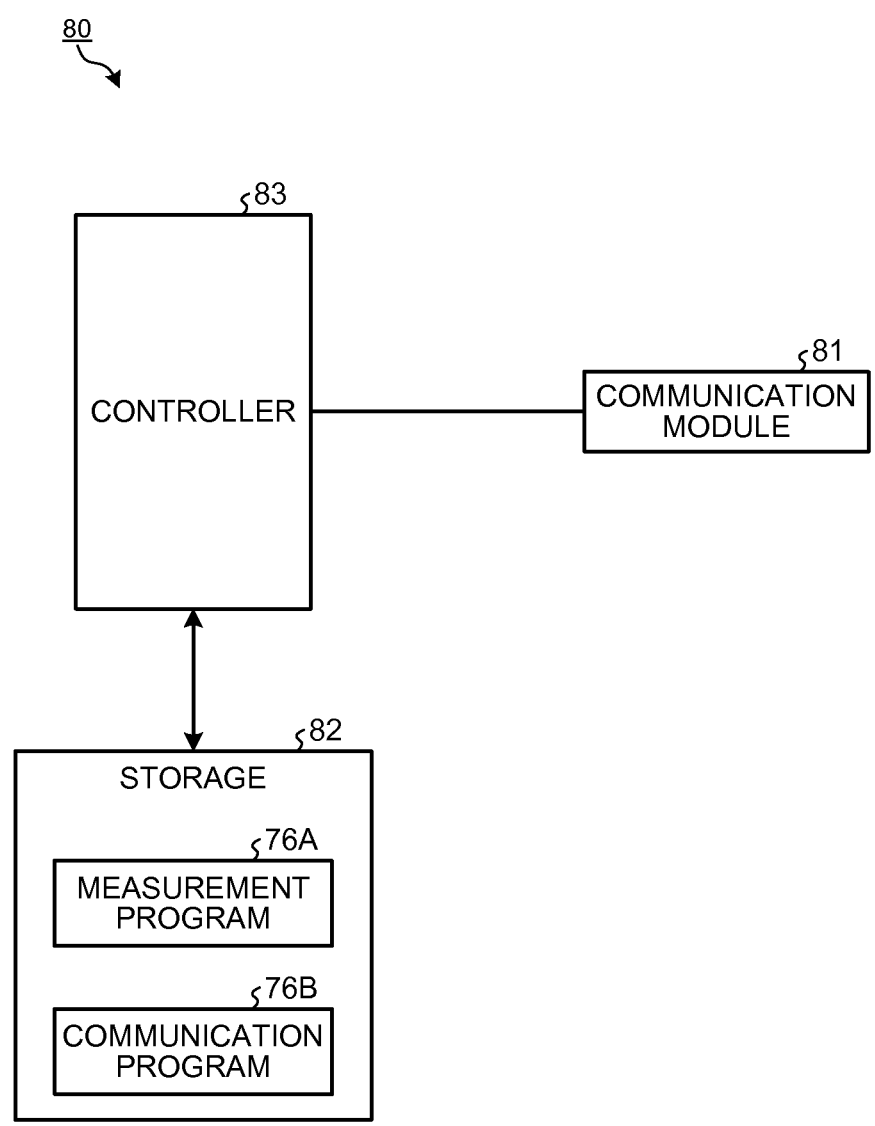
FIG. 11 is a schematic block diagram illustrating functions of a server according to an embodiment of some embodiments.

The server 80 illustrated in FIG. 8 is configured with a complex of one or more devices. The server 80 includes a communication module 81 serving as communication module, a storage 82 serving as a storage module, and a controller 83 serving as a control module as illustrated in FIG. 11.

The communication module 81 serving as the communication module can be a block that undertakes a transceiving function of the server 80. The communication module 81 of an embodiment can function as a member that can receive the operation factor transmitted from the weight scale 70 serving as the measuring device to the outside. The communication module 81 of an embodiment can function as a member that can transmit the operation factor received from the measuring device to the outside. The communication module 81 of the server 80 can support various communication standards such as a LAN port.

The storage 82 serving as the storage module can be a block that undertakes a storage function of the server 80. The storage 82 can function as a member that can store the operation factor received through the communication module 81. The operation factor stored in the storage 82 can be stored in association with the user of the corresponding operation factor. Since the operation factor can be associated with the user, the server 80 can provide an appropriate operation factor to the user who requests transmission of the operation factor.

The storage 82 can store the received operation factor with the date and time at which the operation factor is measured. Since the operation factor can be stored in association with the measurement date and time, the server 80 can provide a more accurate operation factor to the user. Further, since the operation factor can be stored in association with the measurement date and time, the server 80 can transmit a plurality of operation factors to the user to which the operation factor has not been transmitted for a while. By receiving the operation factor associated with the measurement date and time, the user can receive a plurality of operation factors together. When a plurality of operation factors are received together, the user can reduce the number of works of updating the operation factor.

The controller 83 serving as the control module can be a block that undertakes a control function of the server 80. The controller 83 is, for example, configured with a CPU. The controller 83 may be an IC such as an SoC in which another component such as the communication module 82 is integrated. The controller 83 may be configured such that a plurality of ICs are combined. The controller 83 integrally can control the operation of the server 80 such that various kinds of functions are implemented.

Specifically, the server 80 can execute a command included in the program stored in the storage 82 with reference to data stored in the storage 82 as necessary, and can control various components such that various kinds of functions are implemented.

The present disclosure has been described in connection a characteristic embodiment for complete and explicit disclosure. However, claims set forth below are not limited to the above embodiments, and it is obvious that an implementation can be performed to embody all modifications and substitutions that can be derived by those having skill in the art within the scope of basic matters described in the present specification.

In the smartphone 1 of an embodiment, the energy consumption can be calculated based on the weight, but the embodiments are not limited thereto. For example, the smartphone 1 may calculate the energy consumption based on basal metabolic expenditure. The basal metabolic expenditure refers to minimum energy consumption necessary for living. It is possible to more appropriately calculate one-day energy consumption by acquiring the basal metabolic expenditure from the outside including the weight scale 70 and the server 80.

In the smartphone 1 of an embodiment, the energy consumption serving as an example of the calculated activity factor can be displayed on the display screen 60, but the embodiments are not limited thereto. For example, the calculated activity factor may be transmitted to an external device such as a server. When transmitting the activity factor, it is desirable to transmit the activity factor to the server that has received the operation factor.

The present disclosure has been described in detail in connection with a specific embodiment, but it is obvious to those having skill in the art that various changes or modifications can be made.

What is claimed is:

1. A mobile device, comprising:
a motion sensor attached to the mobile device and configured to detect a motion factor for determining movement methods of a user of the mobile device;
a communicator configured to receive a plurality of operation factors used for an operation of an activity factor indicating an activity amount that indicates a body activity of the user and respective dates and times at which the operation factors are measured;
a controller configured to calculate the activity factor indicating the activity amount using (i) the operation factors received through the communicator and (ii) a value based on the motion factor detected by the motion sensor when the operation factors are received; and
a display configured to display a notification screen to notify the activity amount of the user to said user of the mobile device, wherein
the motion sensor includes at least one of an acceleration sensor, a direction sensor, an angular velocity sensor, and an inclination sensor,
the motion factor includes at least one of acceleration acting on the mobile device detected by the acceleration sensor, a geomagnetism orientation detected by the direction sensor, an angular velocity of the mobile device detected by the angular velocity sensor, and inclination of the mobile device detected by the inclination sensor with respect to the gravity direction, and
the display is configured to display to the user,
on a first display area, activity amounts of body activities of the user corresponding to the determined movement methods, wherein
for a first determined movement method having a first coefficient equal to or more than a predetermined value, the display is configured to display, on the first display area, first activity information including (i) the first determined movement method and (ii) the activity amount of the user corresponding to the first determined movement method, for a second determined movement method having a second coefficient less than the predetermined value, the display is configured to display, on the first display area, second activity information including (i) the second determined movement method of the user and (ii) a moving time of the second determined movement method of the user, but without displaying the activity amount of the user corresponding to the second determined movement method, and the first activity information and the second activity information are displayed together, and on a second display area, a duration of each of the body activities of the user and the movement methods corresponding to said body activities, per day in a time series.

2. The mobile device according to claim 1, wherein the controller is configured to calculate the activity factor indicating the activity amount using the value based on the motion factor, the received operation factors, and a coefficient based on the motion factor detected by the motion sensor.

3. The mobile device according to claim 2, wherein the coefficient based on the motion factor indicates intensity of the body activity of the user whose activity factor is operated and differs according to a type of the body activity, and the operation factors include a weight of the user, and the value based on the motion factor includes a period of time of the body activity of the user.

4. The mobile device according to claim 3, wherein the controller is configured to
determine the type of the body activity of the user based on the motion factor, and
determine the coefficient based on the determined type of the body activity of the user.

5. The mobile device according to claim 1, further comprising:
a storage configured to store the operation factors received through the communicator, wherein
the controller is configured to store, in the storage, a first operation factor received through the communicator when the communicator receives the first operation factor and a first date and time at which the first operation factor is measured,
the controller is configured to calculate an activity factor based on the first operation factor and a value based on the motion factor after the first date and time,
the controller is configured to store, in the storage, a second operation factor received through the communicator when the communicator receives the second operation factor and a second date and time at which the second operation factor is measured, after storing the first operation factor in the storage, and
the controller is configured to
calculate an activity factor between the first date and time and the second date and time based on the first operation factor corresponding to the first date and time and the value based on the motion factor, and
calculate an activity factor later than the second date and time based on the second operation factor corresponding to the second date and time and the value based on the motion factor.

6. The mobile device according to claim 1, wherein the communicator is configured to receive the operation factors used for an operation of the activity factor indicating the activity amount from an external device, and the communicator is configured to transmit the activity factor calculated by the controller to the external device.

7. The mobile device according to claim 6, wherein the communicator is configured to receive the operation factors and calculate the activity factor before transmitting the activity factor indicating the activity amount calculated by the controller to the external device.

8. The mobile device according to claim 1, wherein the first determined movement method includes walking, running and riding a bicycle, and the second determined movement method includes a movement using an automobile, a motorcycle, or an airplane.

9. An activity calculation system, comprising:
a measuring device; and
a mobile device, wherein
the measuring device comprises
a measuring sensor configured to measure a plurality of operation factors used for an operation of an activity factor indicating an activity amount that indicates a body activity of a user, and
a first communicator configured to transmit the operation factors measured by the measuring sensor and respective dates and times at which the operation factors are measured, and
the mobile device comprises
a second communicator configured to receive the operation factors and the respective dates and times at which the operation factors are measured from the first communicator of the measuring device,
a motion sensor attached to the mobile device and configured to detect a motion factor for determining movement methods of the user having the mobile device,
a controller configured to calculate the activity factor indicating the activity amount using a value based on the motion factor detected by the motion sensor and the operation factors received through the second communicator, and
a display configured to display a notification screen to notify the activity amount of the user to said user having the mobile device,
the motion sensor includes at least one of an acceleration sensor, a direction sensor, an angular velocity sensor, and an inclination sensor,
the motion factor includes at least one of acceleration working on the mobile device detected by the acceleration sensor, a geomagnetism orientation detected by the direction sensor, an angular velocity of the mobile device detected by the angular velocity sensor, and inclination of the mobile device detected by the inclination sensor with respect to the gravity direction, and
the display is configured to display to the user,
on a first display area, activity amounts of body activities of the user corresponding to the determined movement methods, wherein
for a first determined movement method having a first coefficient equal to or more than a predetermined value, the display is configured to display, on the first display area, first activity information including (i) the first determined movement method and (ii) the activity amount of the user corresponding to the first determined movement method, for a second determined movement method having a second coefficient less than the predetermined value, the display is configured to display, on the first display area, second activity information including (i) the second determined movement method of the user and (ii) a moving time of the second determined movement method of the user, but without displaying the activity amount of the user corresponding to the second determined movement method, and the first activity information and the second activity information are displayed together, and on a second display area, a duration of each of the body activities of the user and the movement methods corresponding to said body activities, per day in a time series.

10. A control method of a mobile device equipped with a motion sensor attached to the mobile device and configured to detect a motion factor for determining movement methods of a user of the mobile device, the control method comprising:

receiving a plurality of operation factors used for an operation of an activity factor indicating an activity amount that indicates a body activity of the user, detected by the motion sensor;

calculating the activity factor indicating the activity amount using (i) the received operation factors and (ii) a value based on the motion factor corresponding to a date and a time corresponding to the operation factors and detected by the motion sensor; and displaying, by a display, a notification screen to notify the activity amount of the user to said user of the mobile device, wherein the motion sensor includes at least one of an acceleration sensor, a direction sensor, an angular velocity sensor, and an inclination sensor, the motion factor includes at least one of acceleration working on the mobile device detected by the acceleration sensor, a geomagnetism orientation detected by the direction sensor, an angular velocity of the mobile device detected by the angular velocity sensor, and inclination of the mobile device detected by the inclination sensor with respect to the gravity direction, and in said displaying, the display displays, to the user, on a first display area, activity amounts of body activities of the user corresponding to the determined movement methods, wherein for a first determined movement method having a first coefficient equal to or more than a predetermined value, the display is configured to display, on the first display area, first activity information including (i) the first determined movement method and (ii) the activity amount of the user corresponding to the first determined movement method, for a second determined movement method having a second coefficient less than the predetermined value, the display is configured to display, on the first display area, second activity information including (i) the second determined movement method of the user and (ii) a moving time of the second determined movement method of the user, but without displaying the activity amount of the user corresponding to the second determined movement method, and the first activity information and the second activity information are displayed together, and on a second display area, a duration of each of the body activities of the user and the movement methods corresponding to said body activities, per day in a time series.

11. A computer program product comprising a non-transitory computer readable storage medium storing thereon computer instructions for a mobile device, the mobile device including a controller, a communicator, and a motion sensor attached to the mobile device and configured to detect a motion factor for determining movement methods of a user of the mobile device, the computer instructions, when executed by the controller, causing the controller to perform operations comprising:

causing the communicator to receive a plurality of operation factors used for an operation of an activity factor indicating an activity amount that indicates a body activity of the user, detected by the motion sensor and respective dates and times at which the operation factors are measured;

causing the controller to calculate the activity factor indicating the activity amount using (i) the operation factors received through the communicator and (ii) a value based on the motion factor detected by the motion sensor when the operation factors are received; and displaying, by a display, a notification screen to notify the activity amount of the user to said user of the mobile device, wherein the motion sensor includes at least one of an acceleration sensor, a direction sensor, an angular velocity sensor, and an inclination sensor, the motion factor includes at least one of acceleration working on the mobile device detected by the acceleration sensor, a geomagnetism orientation detected by the direction sensor, an angular velocity of the mobile device detected by the angular velocity sensor, and inclination of the mobile device detected by the inclination sensor with respect to the gravity direction, and in said displaying, the display displays, to the user, on a first display area, activity amounts of body activities of the user corresponding to the determined movement methods, wherein for a first determined movement method having a first coefficient equal to or more than a predetermined value, the display is configured to display, on the first display area, first activity information including (i) the first determined movement method and (ii) the activity amount of the user corresponding to the first determined movement method, for a second determined movement method having a second coefficient less than the predetermined value, the display is configured to display, on the first display area, second activity information including (i) the second determined movement method of the user and (ii) a moving time of the second determined movement method of the user, but without displaying the activity amount of the user corresponding to the second determined movement method, and the first activity information and the second activity information are displayed together, and on a second display area, a duration of each of the body activities of the user and the movement methods corresponding to said body activities, per day in a time series.

12. An activity calculation system, comprising:
a measuring device;
a server; and
a mobile device, wherein
the measuring device comprises
  a measuring sensor configured to measure a plurality of operation factors used for an operation of an activity factor indicating an activity amount that indicates a body activity of a user, and
  a first communicator configured to transmit the operation factors measured by the measuring sensor and respective dates and times at which the operation factors are measured to the server,
the server comprises a second communicator configured to
  receive the operation factors transmitted from the first communicator of the measuring device, and
  transmit the received operation factors and the respective dates and times at which the operation factors are measured to the mobile device,
the mobile device comprises
  a third communicator configured to receive the operation factors and the respective dates and times at which the operation factors are measured from the second communicator of the server,
  a motion sensor attached to the mobile device and configured to detect a motion factor for determining movement methods of the user having the mobile device,
  a controller configured to calculate the activity factor indicating the activity amount using (i) the operation factors received through the third communicator and (ii) a value based on the motion factor corresponding to the respective date and time corresponding to the operation factors and detected by the motion sensor, and
  a display configured to display a notification screen to notify the activity amount of the user to said user having the mobile device,
the motion sensor includes at least one of an acceleration sensor, a direction sensor, an angular velocity sensor, and an inclination sensor,
the motion factor includes at least one of acceleration working on the mobile device detected by the acceleration sensor, a geomagnetism orientation detected by the direction sensor, an angular velocity of the mobile device detected by the angular velocity sensor, and inclination of the mobile device detected by the inclination sensor with respect to the gravity direction, and
the display is configured to display to the user,
  on a first display area, activity amounts of body activities of the user corresponding to the determined movement methods, wherein
    for a first determined movement method having a first coefficient equal to or more than a predetermined value, the display is configured to display, on the first display area, first activity information including (i) the first determined movement method and (ii) the activity amount of the user corresponding to the first determined movement method,
    for a second determined movement method having a second coefficient less than the predetermined value, the display is configured to display, on the first display area, second activity information including (i) the second determined movement method of the user and (ii) a moving time of the second determined movement method of the user, but without displaying the activity amount of the user corresponding to the second determined movement method, and
    the first activity information and the second activity information are displayed together, and
  on a second display area, a duration of each of the body activities of the user and the movement methods corresponding to said body activities, per day in a time series.

* * * * *